United States Patent

Mori et al.

[11] Patent Number: 5,835,631
[45] Date of Patent: Nov. 10, 1998

[54] METHOD AND APPARATUS FOR EVALUATING AN INDIVIDUAL USING CHARACTER RECOGNITION PROCESSING OF INPUT HANDWRITTEN CHARACTERS

[75] Inventors: Shigeki Mori, Koshigaya; Katsuhiko Sakaguchi, Kawasaki; Kazuhiro Matsubayashi, Yokohama; Tsunekazu Arai, Tama; Takashi Harada, Yokohama; Eiji Takasu, Yokohama, all of Japan

[73] Assignee: Canon Kabushiki Kaisha, Tokyo, Japan

[21] Appl. No.: 511,629

[22] Filed: Aug. 7, 1995

Related U.S. Application Data

[63] Continuation of Ser. No. 114,341, Sep. 1, 1993, abandoned.

[30] Foreign Application Priority Data

Sep. 11, 1992 [JP] Japan .................................. 4-243484

[51] Int. Cl.⁶ ............................................... G06K 9/00
[52] U.S. Cl. ......................... 382/181; 382/187; 382/313
[58] Field of Search ................................... 382/181, 187, 382/188, 189, 203, 313, 314, 315, 321; 434/349, 356, 359, 362

[56] References Cited

U.S. PATENT DOCUMENTS

| | | | |
|---|---|---|---|
| 4,972,496 | 11/1990 | Sklarew | 382/13 |
| 5,102,341 | 4/1992 | Koslin | 434/353 |
| 5,180,309 | 1/1993 | Egnor | 434/323 |
| 5,481,626 | 1/1996 | Matsubayashi | 382/315 |

FOREIGN PATENT DOCUMENTS

| | | | |
|---|---|---|---|
| 0042487 | 12/1981 | European Pat. Off. | G09B 11/00 |
| 0254561 | 1/1988 | European Pat. Off. | G06F 3/02 |
| 2301404 | 7/1974 | Germany . | |

OTHER PUBLICATIONS

"Measurements of Graphological Elements By Means Of The Optical Fourier Transform", G. Brautti, et al., Alta Frequenza, vol. 47, Nr. 3, Mar. 1978, pp. 215–218 (abstract only).

"Quantification Of Tremor With A Digitising Tablet", Elble, et al., Journal Of Neuroscience Methods, vol. 32, Nr. 3, Jun. 1990, pp. 193–198 (abstract only).

"A Device For Recording Human Handwriting Or Other Tracing Movements", Yasuhara, Conference IMEKO V., Versailles, France, May 1970, pp. 14–17 (abstract only).

*Primary Examiner*—Phuoc Tran
*Attorney, Agent, or Firm*—Fitzpatrick, Cella, Harper & Scinto

[57] ABSTRACT

A method and apparatus for analyzing handwritten characters include inputting a handwritten character, recognizing the handwritten character, and extracting feature data of the handwritten character. The extracted feature data is compared with and identified to prestored feature data in memory. The prestored feature data is stored with respective handwritten character analysis data. In the case that the extracted feature data has been identified, respective handwritten character analysis data is output. On the other hand, in the case that the extracted feature data has not been identified, a message is output.

13 Claims, 3 Drawing Sheets

FIG.3
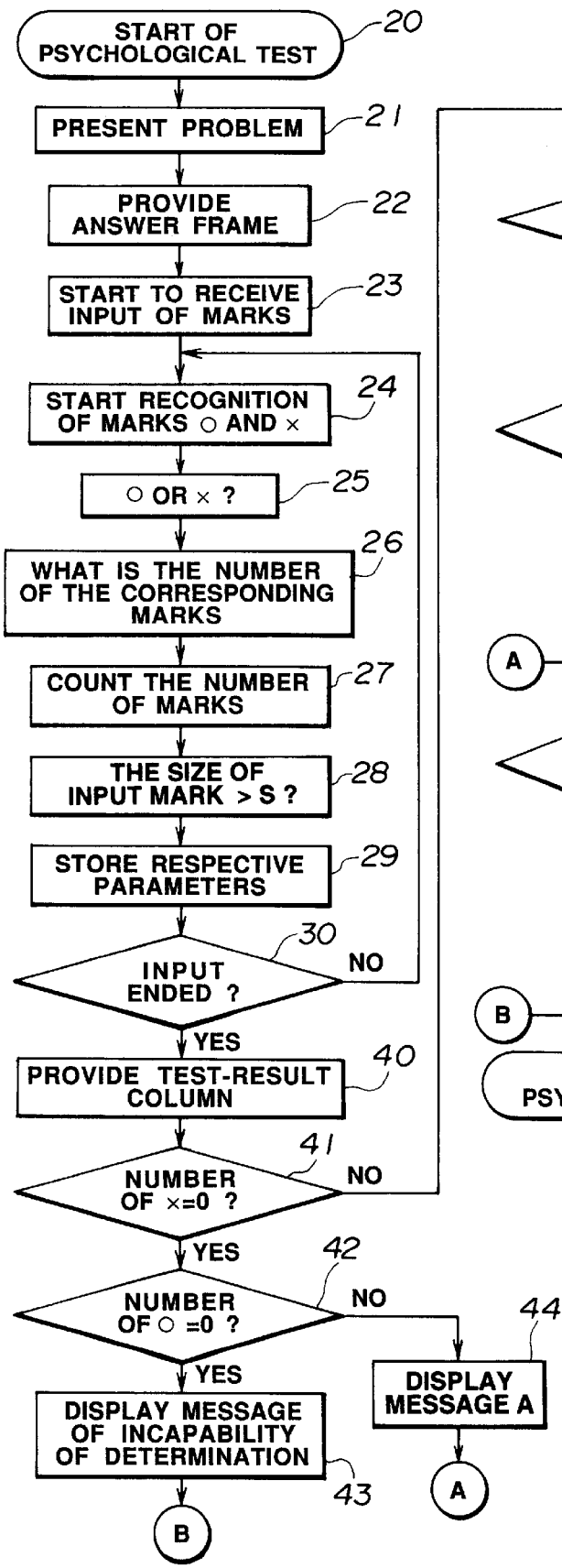
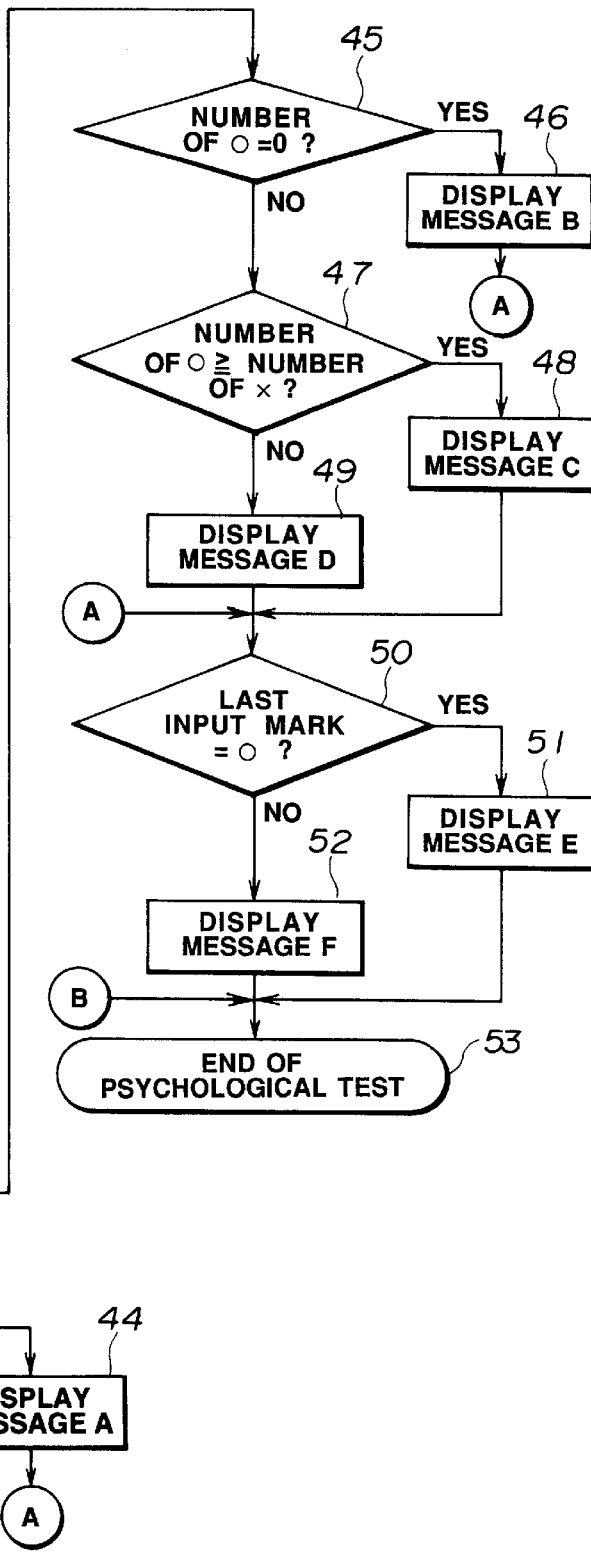

METHOD AND APPARATUS FOR EVALUATING AN INDIVIDUAL USING CHARACTER RECOGNITION PROCESSING OF INPUT HANDWRITTEN CHARACTERS

This application is a continuation of application Ser. No. 08/114,341 filed Sep. 1, 1993, now abandoned.

BACKGROUND OF THE INVENTION

1. Field of the Invention

This invention relates to a method and an apparatus for recognizing handwritten characters, pictures or drawings input as coordinate data, extracting characteristics of the data, and evaluating an operator based on the recognized data and extracted characteristics.

2. Description of the Related Art

Conventionally, personal information, such as psychological information, has been obtained by evaluating a person's responses to a set of questions. There are several disadvantages to this method of obtaining personal information. For example, because a trained evaluator must be on hand to pose questions and evaluate a person's responses, a person being evaluated might be reluctant to answer questions truthfully. Such behavior on the part of the person being evaluated can often result in incorrect personal information being obtained.

Incorrect personal information can also be obtained when an evaluator misinterprets data or when an evaluator's subjective experiences cloud his or her interpretation of the data. For example, an evaluator's like or dislike of a person being evaluated can affect the evaluator's interpretation of the person's answers to questions. As a result, incorrect personal information can be obtained.

In addition to the inaccuracies inherent in the conventional method of obtaining personal information discussed above, conventional methods of obtaining personal information can also be very expensive and inconvenient.

SUMMARY OF THE INVENTION

According to the present invention, when a person being tested answers questions posed by the invention by inputting answers using a stylus pen to a pen-based computer (hereinafter "PBC") having a handwriting input/output apparatus, the invention recognizes handwritten input characters, pictures, and drawings by extracting characteristics of the handwritten input characters, pictures, or drawings based on a result of a recognition operation. The invention compares the extracted characteristics with database information and, based on the results of the comparison, outputs information about the person being tested.

Since handwritten data for evaluating personal information is input by coordinate input, detailed data characteristics, such as input order of the input data, shapes of the input data, and positions of the input data, can be extracted. As a result, broader range of personal information can be obtained.

In one aspect of the invention, a method and apparatus for analyzing handwritten characters includes inputting handwritten information, extracting characteristics of the input handwritten information, and outputting information corresponding to the extracted characteristics of the input information.

In another aspect of the invention, a method and apparatus for inputting/outputting information includes presenting a problem to a user, inputting an answer corresponding to the problem, and recognizing characters, pictures, or drawings included in the answer and time-serially storing information relating to the state of the recognized items. In the information input/output method and apparatus, comparative calculation of the stored information is performed and specific character information is output as a result of the comparative calculation.

In another aspect of the invention, a method and apparatus for analyzing handwritten characters includes inputting a handwritten character, recognizing the handwritten character, and extracting feature data of the handwritten character. The extracted feature data is compared and identified with prestored feature data in memory. The prestored feature data is stored with respective handwritten character analysis data. In the case that the handwritten characters are identified, respective handwritten character analysis data is output. On the other hand, in the case that the extracted feature data has not been identified, a message is output.

BRIEF DESCRIPTION OF THE DRAWINGS

FIG. 3 is a flowchart illustrating a psychological testing routine of the present embodiment.

DESCRIPTION OF THE PREFERRED EMBODIMENTS

Figure 1:
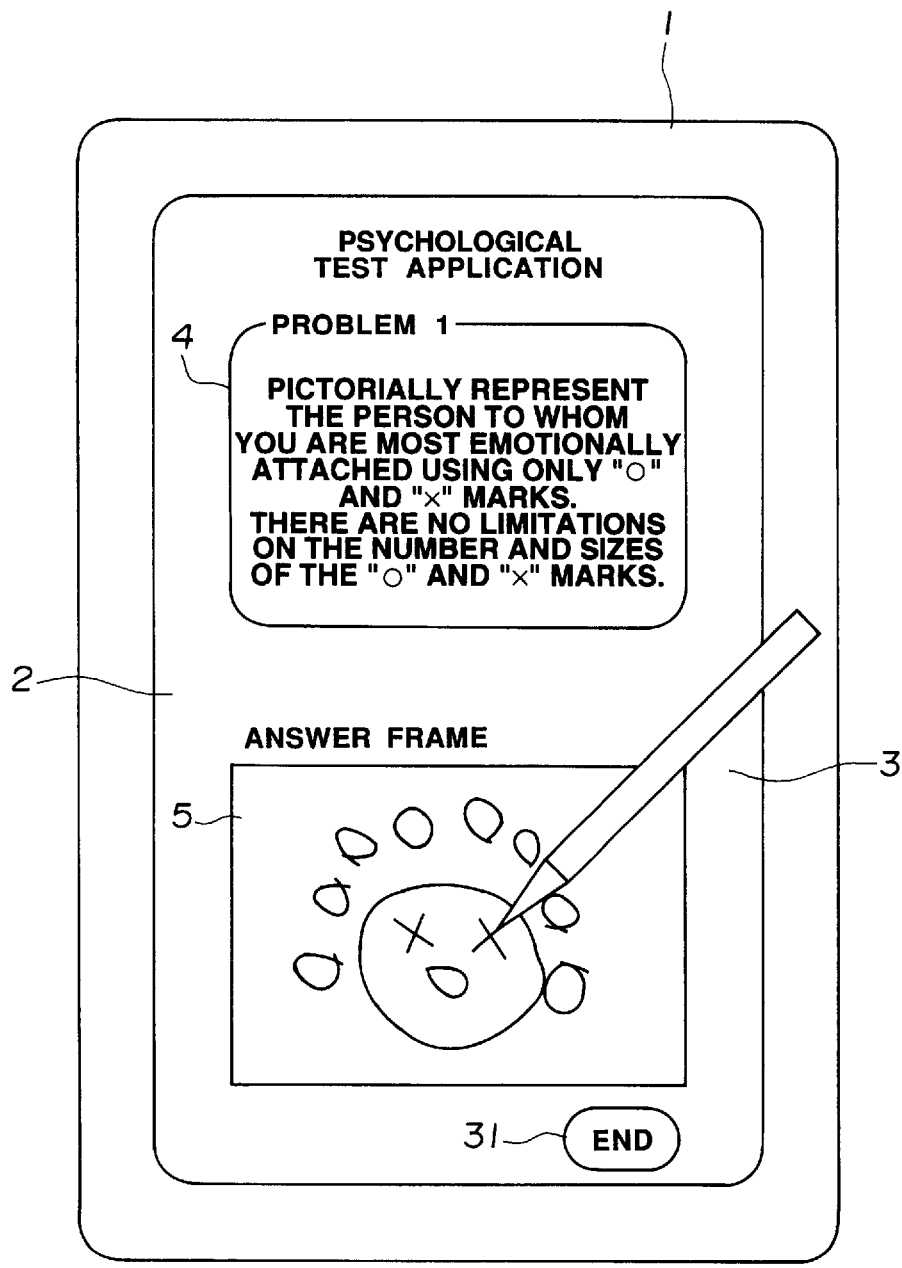
FIG. 1 is an illustration of an external appearance of a psychological testing apparatus according to an embodiment of the present invention.

FIG. 1 is an illustration of an embodiment of the present invention showing an external appearance of an apparatus for performing psychological tests using a PBC. In FIG. 1, reference numeral 1 represents a main body of the PBC. Main body 1 has a size, shape, and external appearance such that it can be easily carried to a testing site by an individual. Integrated input/output unit 2 serves as the input/output unit of main body 1. Stylus pen 3 is used to input handwritten information into integrated input/output unit 2. Reference numeral 4 represents a problem display portion of integrated input/output unit 2. Problem display portion 4 is used to display a psychological test problem to a user. After an answer to the problem has been completed and an end key (to be described later) has been touched, problem display portion 4 displays the result of the psychological test. Reference numeral 5 represents an answer display portion of integrated input/output unit 2 where an answer to a psychological test problem is displayed. End key 31 is a soft key to be touched when an answer input to answer display portion 5 has been completed.

Figure 2:
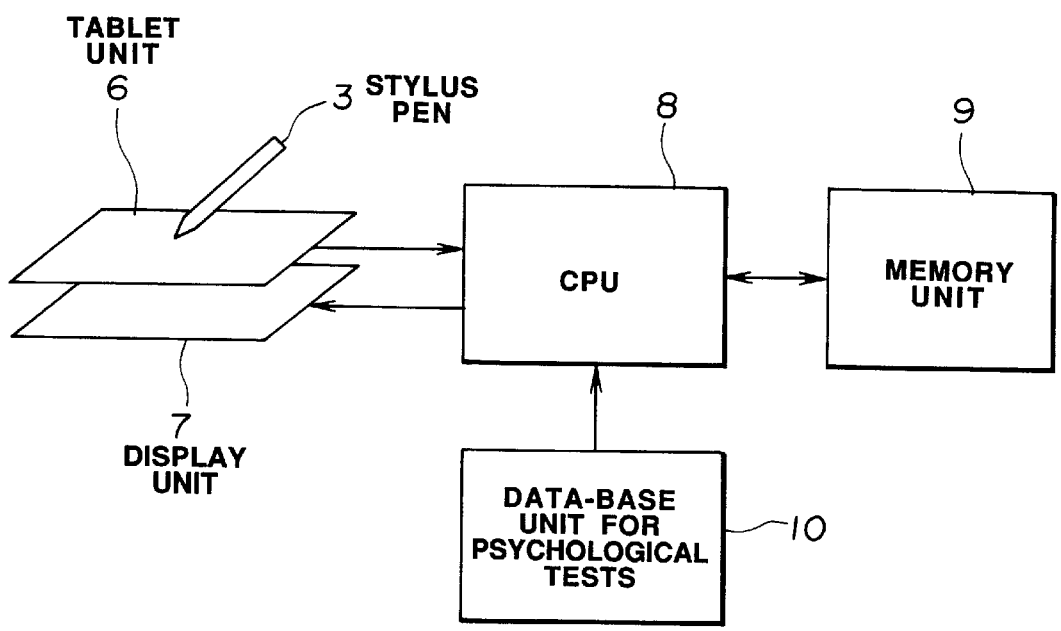
FIG. 2 is a block diagram showing the configuration of the psychological testing apparatus shown in FIG. 1.

FIG. 2 is a block diagram illustrating the internal configuration of the psychological testing apparatus of the present embodiment. Stylus pen 3 inputs handwritten information onto tablet unit 6. Display unit 7 constitutes integrated input/output unit 2 and tablet unit 6. CPU (central processing unit) 8 controls, calculates and processes various kinds of information. Memory unit 9 stores recognized input data, control programs for processing performed by CPU 8, and results of calculation. Memory unit 9 includes a ROM (read-only memory) and a RAM (random access memory). Data-base unit 10 stores information and data needed to perform psychological tests. Data-base unit 10 may comprise a memory detachable from main body 1 of the PBC, or data-base unit 10 may comprise an independent external unit.

FIG. 3 is a flowchart illustrating the processing of psychological tests according to the present embodiment. In FIG. 3, step 20 represents the starting point of a psychological test. In step 21, a problem is presented to a user. In step 22, an answer frame is provided. In step 23, "○" and "x" marks are input by the user. In step 24, "○" and "x" marks are recognized. In step 25, it is determined whether the input mark is "○" or "x". In step 26, the number of corresponding input marks is determined. In step 27, the number of "○" or "x" marks is counted. In step 28, the size of an input mark is compared with a constant S. In step 29, respective parameters determined in steps 25 through 28 are stored. In step 30, it is determined if the input of an answer to the problem presented in step 21 has ended. In step 40, a column for displaying the result of the psychological test is provided. In step 41, it is determined if the number of input "x" marks equals zero. In step 42, it is determined if the number of input "○" marks equals zero. In step 43, the message of incapability of determination is displayed when no data has been input, or when the content of the input data could not be determined. In step 44, message A is displayed when the input data includes only "○" marks. In step 45, it is determined if the number of input "○" marks equals zero. In step 46, message B is displayed when the input data includes only "x" marks, i.e., the number of "x" marks does not equal zero in step 41 and the number of "○" marks equals zero in step 45. In step 47, the number of "○" marks is compared to the number of "x" marks to determine if the number of "○" marks is greater than or equal to the number of "x" marks. In step 48, message C is displayed when the number of "○" marks is greater than or equal to the number of "x" marks. In step 49, message D is displayed when the number of "○" marks is less than the number of "x" marks. In step 50, it is determined if the last input mark is an "○" mark. In step 51, message E is displayed when the last input mark is an "602" mark. In step 52, message F is displayed when the last input mark is an "x" mark. Step 53 represents the end of the psychological testing routine.

Next, the processing of the flowchart shown in FIG. 3 will be described with reference to the PBC shown in FIG. 1 and the block diagram shown in FIG. 2.

Psychological testing is started in the PBC shown in FIG. 1. The psychological testing routine stored in memory unit 9 is initiated in step 20 shown in FIG. 3 to start a psychological test. In step 21, a psychological test problem from data-base unit 10 is displayed on problem display portion 4 of display unit 7 shown in FIG. 1. In the present embodiment, as illustrated in FIG. 1, the problem displayed is: "Pictorially represent the person to whom you are most emotionally attached using only "○" and "x" marks. There are no limitations on the number and sizes of the "○" and "x" marks. In step 22, the problem shown in FIG. 1 is displayed on answer frame 5, set on integrated input/output unit 2 of main body 1 of the PBC, and the operator is notified that the answer frame has been provided, for example, by displaying the frame. In step 23, the operator begins inputting marks on answer frame 5 using stylus pen 3. In step 24, the process of recognizing "○" or "x" marks input on answer frame 5 is started. In step 25, it is determined if the recognized mark is an "○" or an "x" mark. In step 26, the total number of corresponding input marks is determined. The results of the above-described determination operations are stored in memory unit 9. In step 27, the number of corresponding marks is counted. In step 28, the size of a mark input in step 23 is compared with a constant S. In step 29, the results determined in steps 24 through 28 and the positions of the input marks are stored in data-base unit 10. In step 30, end key 31, comprising a soft key, is touched to determine if the answer to the problem has been completed. If, in step 30, it is determined that the answer to the problem has not been completed, the process returns to step 24. If it is determined, in step 30, that the answer to the problem has been completed, the process proceeds to step 40. In step 40, the column for displaying the psychological test result is provided. In step 41, the total number of input "x" marks is determined. If the total number of "x" marks equals zero, the process proceeds to step 42. If the total number of "x" marks does not equal zero, the process proceeds to step 45. In step 42, the total number of input "○" marks is determined. If the total number of "○" marks also equals zero in step 42, the process proceeds to step 43 where the message of incapability of determination indicating that no marks have been input is displayed on display unit 7. In such a case, the process proceeds to step 53, where the psychological testing routine is terminated. The message of incapability of determination and messages A through F (to be described later) are stored in data-base unit 10. Each of these messages is displayed on display unit 7. If the total number of input "○" marks does not equal zero in step 42, then all input marks are "○" marks. In such a case, message A is displayed in step 44, and the process proceeds to step 50. If the total number of input "x" marks does not equal zero in step 41, the process proceeds to step 45 where it is determined if the total number of input "○" marks equals zero. If the total number of input "○" marks equals zero in step 45, then all input marks are "x" marks. In such a case, message B is displayed in step 46, and the process proceeds to step 50. If the total number of "○" marks does not equal zero in step 45, the process proceeds to step 47 where the total number of input "○" marks is compared with the total number of input "x" marks. If the total number of "○" marks is greater than or equal to the total number of "x" marks in step 47, message C is displayed in step 48, and the process proceeds to step 50. If the total number of "x" marks is greater than the total number of "○" marks in step 47, message D is displayed in step 49, and the process proceeds to step 50. In step 50, it is determined if the last input mark is an "○" mark. If the last input mark is an "○" mark in step 50, message E is displayed in step 51. In such a case, the process proceeds to step 53 where the psychological testing routine is terminated. If the last input mark is not an "○" mark in step 50, message F is displayed in step 52. In such a case, the process proceeds to step 53 where the psychological test routine is terminated.

The present invention has many advantages over the prior art. For example, as described above, according to the present invention, it is possible to perform an accurate psychological test by extracting characteristics of input marks such as the number of marks and input order of the marks by using character recognition means in the PBC to recognize the marks and exactly and time serially storing various parameters of the recognized marks. An additional advantage of the present invention is the portability of the handwritten character analyzer which permits a psychological test to be performed anywhere, thereby eliminating the need for a fixed testing site, and allowing a person being tested to undergo the test in a relaxed atmosphere. Furthermore, since the present invention eliminates the need for a trained psychologist, a person taking a psychological test is assured greater privacy.

In the above-described embodiment, a data-base unit for psychological tests is mounted within one PBC to operate the psychological testing apparatus. However, psychological-test data-base information may be provided as on-line information from a network. It is therefore possible to utilize a more specialized and detailed psychological-test data base such as one provided, for example, by a counselor specialized in psychological tests, without sacrificing a relaxed testing environment, and while maintaining detailed and correct test results. By using on-line information, it is also possible to perform an interactive psychological test having the benefits of a conventional test; i.e., interaction with a trained counselor, without the detriments of a conventional test; i.e., possible intimidation of a patient by a councelor.

The present invention is not limited to psychological test apparatuses. For example, the present invention may also be applied, for example, to correction of written calligraphic characters, by replacing the above-described psychological-test data base with a calligraphic-character data base. In fact, the present invention may be applied to any drawing operation that requires learning or training from standard samples.

What is claimed is:

1. A method for evaluating an individual based on the individual's response, comprising the steps of:

inputting a plurality of marks;

extracting data of a number of a predetermined kind of mark included in the input marks; and outputting a different message in accordance with the extracted data of the number and the kind of mark.

2. A method according to claim 1, wherein, in the inputting step, the plurality of marks are input from a tablet.

3. A method according to claim 1, further comprising the step of displaying the output different message as a character pattern.

4. A method according to claim 1, further comprising the step of storing handwritten character characteristic information and evaluations corresponding to the stored handwritten character characteristic information in a database.

5. A method according to claim 1, wherein said mark is handwriting data.

6. A method according to claim 1, further comprising the step of:

determining a kind of the mark by recognizing said input mark.

7. A method according to claim 1, further comprising the steps of:

judging a kind of mark to be input at a predetermined timing; and outputting a different message in accordance with the judged kind.

8. An apparatus for evaluating an individual based on the individual's response, comprising:

means for inputting a plurality of marks;

characteristic extraction means for extracting data of the number of a predetermined kind of mark included in the input marks; and means for outputting a different message in accordance with the extracted data of the number and the kind of mark.

9. An apparatus according to claim 8, wherein the plurality of marks are input from a tablet.

10. An apparatus according to claim 8, further comprising a display device for displaying the output different message as a character pattern.

11. An apparatus according to claim 8, further comprising a database for storing handwritten character characteristic information and for storing corresponding evaluations.

12. An apparatus according to claim 11, wherein the database is detachable from the main body of the device.

13. A computer-readable memory medium storing computer-executable process steps for evaluating an individual based on the individual's response, the steps comprising:

an inputting step to input a plurality of marks;

an extracting step to extract data of the number of a predetermined kind of mark included in the input marks; and an outputting step to output a different message in accordance with the extracted data of the number and the kind of mark.

* * * * *